(12) United States Patent
Likavec et al.

(10) Patent No.: US 6,248,890 B1
(45) Date of Patent: Jun. 19, 2001

(54) NAPHTHALIMIDE DIESTER FLUORESCENT TRACERS HAVING IMPROVED SOLUBILITY AND FLUORESCENCE

(75) Inventors: Wayne R. Likavec, Parma; Thomas C. DiPietro, Medina, both of OH (US)

(73) Assignee: Day-Glo Color Corp., Cleveland, OH (US)

( * ) Notice: Subject to any disclaimer, the term of this patent is extended or adjusted under 35 U.S.C. 154(b) by 0 days.

(21) Appl. No.: 09/178,956

(22) Filed: Oct. 26, 1998

(51) Int. Cl.[7] .......................... C09B 57/08; C07D 221/06; C09K 3/18; C09K 11/06
(52) U.S. Cl. .................. 546/100; 8/568; 252/70; 252/79; 252/300.16; 252/964
(58) Field of Search .................. 546/100; 8/568; 252/964, 70, 79, 300.16

(56) References Cited

U.S. PATENT DOCUMENTS

| | | | |
|---|---|---|---|
| 3,362,958 | * 1/1968 | Schellhammer et al. | 546/100 |
| 4,172,202 | * 10/1979 | Papenfuhs | 546/100 |
| 4,758,366 | 7/1988 | Parekh, I | 252/68 |
| 5,149,453 | 9/1992 | Parekh, II | 252/68 |
| 5,357,782 | 10/1994 | Henry, I | 73/40.7 |
| 5,421,192 | 6/1995 | Henry, II | 73/40.7 |
| 5,858,930 | 1/1999 | Desai et al. | 508/261 |

FOREIGN PATENT DOCUMENTS

| | | |
|---|---|---|
| 0469018 | * 10/1950 | (CA) . |
| 1816787 | * 5/1993 | (SU) . |
| WO 98/31752 | 7/1998 | (WO) . |

OTHER PUBLICATIONS

CA Selects: Colorants & Dyes, Issue 21, 1998, "Fluorescent naphthalimide dyes and their use as fluid visualizing agents" by Utecht, et al.
Pape et al, C.R. Aead, Sc. Paris, vol. 284, pp. 561–564 (1977).*

* cited by examiner

Primary Examiner—Floyd D. Higel
(74) Attorney, Agent, or Firm—Calfee, Halter & Griswold, LLP

(57) ABSTRACT

A fluorescent naphthalimide diester dye that is miscible or soluble in a variety of organic compounds such as, for example, mineral oil, polyalkylene glycols, polyolesters, motor oil, gear oil, synthetic oils, and polyalphaolefins, is provided. The fluorescent naphthalimide diester is useful as a tracer to detect leaks within a fluid systems such as, for example, refrigerant systems, transmission systems, and hydraulic systems. The fluorescent naphthalimide diester dye is comprised of a chromophore having the following structure:

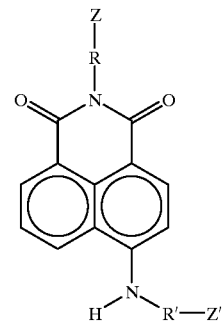

wherein: Z and Z' are the same or different, and are esters attached to saturated or unsaturated linear or branched hydrocarbon chains attached thereto, having from 8 to 24 carbon atoms in length, preferably from 12 to 22 carbon atoms in length, most preferably from 16 to 20 carbon atoms in length, and from 1 to 4 double bonds, most preferably 2 to 3 double bonds. R and R' are saturated, linear hydrocarbon chains, having from 2 to 10 carbon atoms in length, preferably from 2 to 8 carbon atoms in length, most preferably from 3 carbon atoms in length. Z and Z' are preferably fatty acids. The invention also relates to methods of making and using the fluorescent naphthalimide diester dye, as well as to fluorescent naphthalimide diester dye tracers.

23 Claims, No Drawings

NAPHTHALIMIDE DIESTER FLUORESCENT TRACERS HAVING IMPROVED SOLUBILITY AND FLUORESCENCE

BACKGROUND OF THE INVENTION

Fluorescent tracers have been employed to detect leaks in fluid systems such as refrigeration systems, which utilize hydrocarbon refrigerants and lubricants. The site of a leak the refrigerants and refrigerant lubricants which contain the fluorescent tracer escape; they are visible when illuminated with light having wavelengths in the range of 300 to 450 nanometers.

The refrigerant are typically hydrofluorocarbons, hydrochlorofluorocarbons, and mixtures thereof. Common refrigeration lubricants are polyalkylene glycols, polyolesters, mineral oil, polyalphaolefins, and synthetic hydrocarbons.

Traditionally, the typical fluorescent dyes that have been used in fluroescent tracers for refrigeration systems are rhodamine B, Fluorescent Yellow 133SC, auramine B and certain conventional naphthalimide dyes. Some of these dyes are unstable at high temperatures and may be converted to tars, which plug the system. Other dyes have low solubility in the refrigerants and refrigerant lubricants which results in aggregates of precipitated dye circulating through the system. Some of these dyes, while showing good initial solubility in the refrigerants and refrigerant lubricants, tend to be unstable over storage and operation time thus resulting in aggregates of precipitated dye circulating through the system. These aggregates may clog the refrigeration system.

Conventional naphthalimide dyes are fluorescent in polyalkylene glycols, and other polar lubricants. However, naphthalimide dyes have limited solubility in the polar lubricants, and very low solubility in non-polar lubricants such as mineral oil, synthetic oil, and motor oil. The fluorescence of the naphthalimide dyes is often severely limited by the poor solubility. Furthermore, the naphthalimide dyes require long mixing times and/or elevated temperatures to dissolve the dye into the lubricant. Dissolution at elevated temperatures results in solutions that are supersaturated at room temperature. These supersaturated solutions tend to precipitate dye either in the lubricant during shelf storage, or in the refrigerant system during long term operation. The presence of precipitated dye tends to decrease the fluorescence of the solution, thus reducing its effectiveness, and also tends to clog the refrigerant system.

A fluorescent dye that is soluble in refrigerants and refrigerant lubricants, chemically stable at high temperatures and provides improved shelf stability is desirable.

SUMMARY OF THE INVENTION

The present invention provides a highly fluorescent naphthalimide diester dye that is miscible or soluble in a variety of polar and non-polar organic liquids such as, for example, mineral oil, polyalkylene glycols, polyolesters, motor oil, gear oil, synthetic oils, and polyalphaolefins. The fluorescent naphthalimide diester is useful as a tracer to detect leaks within a fluid systems such as, for example, refrigerant systems, transmission systems, and hydraulic systems. The fluorescent naphthalimide diester dye is stable during storage and operation time, thus eliminating the dye precipitation problem associated with conventional naphthalimide dye tracers. The fluorescent naphthalimide diester dye is stable at high temperatures. Preferably, the fluorescent naphthalimide diester dye is a liquid at room temperature.

The fluorescent naphthalimide diester dye is comprised of a chromophore having the following structure:

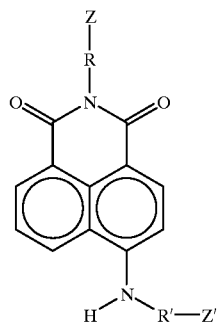

wherein:

Z and Z' are esters having a saturated or unsaturated, linear or branched, hydrocarbon chain attached thereto, having from 8 to 24 carbon atoms in length, preferably from 12 to 22 carbon atoms in length, most preferably from 16 to 20 carbon atoms in length, and from 1 to 4 double bonds, most preferably 2 to 3 double bonds;

R and R' are saturated, linear hydrocarbon chains, having from 2 to 10 carbon atoms in length, preferably from 2 to 8 carbon atoms in length, most preferably from 3 carbon atoms in length. R is attached to Z by the ester linkage, and R' is attached to Z' by the ester linkage.

Z and Z' are preferably fatty acid esters. Preferred linear fatty acid esters are, for example the esters of: decanoic acid, nonanoic acid, octanoic acid, citronellic acid, undecanoic acid, lauric acid, tridecanoic acid, myristoleic acid, myristic acid, pentadecanoic acid, palmitoleic acid, palmitic acid, heptadecanoic acid, linolenic acid, linoleic acid, oleic acid, nonadecanoic acid, cis-11-eicosanoic acid, eicosanoic acid, 11, 14-eicosadienoic acid, erucic acid, docosanoic acid, and behenic acid. Preferred branched acids are, for example: isononanoic acid, neoheptanoic acid, neononanoic acid, neodecanoic acid, iso-octanoic acid, neo octanoic acid, and isostearic acid.

The invention also relates to methods of making and using the fluorescent naphthalimide diester dye, as well as to fluorescent naphthalimide diester tracers.

DETAILED DESCRIPTION OF THE INVENTION

The present invention provides a fluorescent naphthalimide diester dye that is miscible in organic compounds used in fluid systems. As used herein "fluid" means liquid and gas. Fluid systems are closed systems which contain a fluid; examples are refrigerant systems, hydraulic systems, transmission systems, heating systems, ventilating systems, and systems which utilize petrochemical oils, and which utilize hydrocarbon lubricant.

The fluorescent naphthalimide diester dye is soluble or miscible in a variety of polar and non-polar organic liquids such as refrigerant lubricants and refrigerants, mineral oil, polyalkylene glycols, coolants, polyolesters, motor oil, gear oil, transmission fluid, synthetic oils, and polyalphaolefins. The fluorescent naphthalimide diester dye is useful to detect leaks within a fluid system. The fluorescent naphthalimide diester dye is highly fluorescent, possesses excellent solution stability during storage and operation, and is stable at high temperatures.

The Fluorescent Naphthalimide Diester Chromophore

The fluorescent naphthalimide diester chromophore has the following structure:

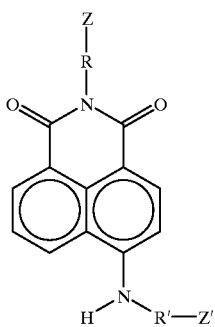

wherein:
Z and Z' are esters having a saturated or unsaturated, linear or branched, hydrocarbon chain attached thereto, having from 8 to 24 carbon atoms in length, preferably from 12–22 carbon atoms in length, most preferably from 16 to 20 carbon atoms in length, and from 1 to 4 double bonds, most preferably 2 to 3 double bonds;
R and R' are saturated, linear hydrocarbon chains, having from 2 to 10 carbon atoms in length, preferably from 2 to 8 carbon atoms in length, most preferably from 3 carbon atoms in length. R is attached to Z by the ester linkage, and R' is attached to Z' by the ester linkage.

Z and Z' are preferably esters of fatty acids. Preferred linear fatty acid esters are, for example esters of: decanoic acid, nonanoic acid, octanoic acid, citronellic acid, undecanoic acid, lauric acid, tridecanoic acid, myristoleic acid, myristic acid, pentadecanoic acid, palmitoleic acid, palmitic acid, heptadecanoic acid, linolenic acid, linoleic acid, oleic acid, nonadecanoic acid, cis-11-eicosanoic acid, eicosanoic acid, 11, 14-eicosadienoic acid, erucic acid, docosanoic acid, and behenic acid. Preferred branched acids are, for example: isononanoic acid, neoheptanoic acid, neononanoic acid, neodecanoic acid, iso-octanoic acid, neo octanoic acid, and isostearic acid.

The fluorescent naphthalimide diester chromophore has a number average molecular weight of from about 570 to about 2000, preferably from about 600 to about 1500, more preferably from about 700 to about 1100. At molecular weights above about 2000, the fluorescent naphthalimide diester chromophore looses solubility, particularly in nonpolar materials such as mineral oil. At molecular weights below about 570, the fluorescent naphthalimide diester chromophore tends to crystallize and loose solubility.

The Fluorescent Naphthalimide Diester Dye

The fluorescent naphthalimide diester dye is comprised of at least one fluorescent naphthalimide diester chromophore. Where a single chromophore is used it is preferred that Z or Z' or both are the ester of oleic acid, the ester of linolenic acid or the ester of linoleic acid.

Preferably, the fluorescent naphthalimide diester dye is a mixture of fluorescent naphthalimide diester chromophores.

In one embodiment, the fluorescent naphthalimide diester dye is preferably a mixture of fluorescent naphthalimide diester chromophores wherein which comprises at least 50%, more preferably at least 60%, even more preferably at least 70%, most preferably at least about 80% fluorescent naphthalimide diester chromophores in which Z or Z', or both, are selected from the group consisting of: ester of linoleic acid, ester of linolenic acid, ester of oleic acid and mixtures thereof.

In another embodiment, the fluorescent naphthalimide diester dye is preferably a mixture of fluorescent naphthalimide diester chromophores wherein Z or Z' or both, are selected from the group consisting of the ester of linoleic acid, the ester of oleic acid, the ester of linolenic acid or mixtures thereof. Preferably the fluorescent naphthalimide diester dye comprises: from about 0.1% to about 99.9%, more preferably from about 20% to about 90% of the ester of oleic acid; from about 0.1% to about 99.9%, more preferably from about 20% to about 90% of the ester of linoleic acid; from about 0.1% to about 99.9%, more preferably from about 20% to about 90%, of the ester of linolenic acid.

In one embodiment, the fluorescent naphthalimide diester dye is preferably a mixture of fluorescent naphthalimide diester chromophores wherein Z or Z' or both, comprise: from about 0.1% to about 20%, more preferably from about 1% to about 6%, most preferably about 3% of the ester of myristic acid; from about 0.1% to about 20%, more preferably from about 1% to about 10%, most preferably about 1% of the ester of margaric acid; from about 0.1% to about 20%, more preferably from about 1% to about 10%, most preferably about 2% of the ester of stearic acid; from about 1% to about 20%, more preferably from about 1% to about 10%, most preferably about 2% of the ester of myristoleic acid; from about 0.1% to about 90%, more preferably from about 0.5% to about 70%, most preferably about 1% of the ester of linolenic acid; from about 1% to about 90%, more preferably from about 20% to about 70%, most preferably about 69% of the ester of oleic acid; from about 16 to about 90%, more preferably from about 5% to about 85%, most preferably about 10% of the ester of linoleic acid; from about 0.1% to about 20%, more preferably from about 1% to about 10%, most preferably about 6% of the ester of palmitoleic acid;, and about from about 0.1% to about 20%, more preferably from about 1% to about 10%, most preferably 6% of the ester of palmitic acid.

In another embodiment, the fluorescent naphthalimide diester dye is preferably a mixture of fluorescent naphthalimide diester chromophores wherein Z or Z' or both, comprise: from about 0.1% to about 20%, more preferably from about 1% to about 8%, most preferably about 4% of the ester of steric acid; from about 10% to about 90%, more preferably from about 20% to about 70%, most preferably about 24% of the ester of oleic acid; about from about 20% to about 90%, more preferably from about 40% to about 70%, most preferably 53% of the ester of linoleic acid; about from about 1% to about 90%, more preferably from about 3% to about 70%, most preferably about 6% of the ester of linolenic acid; from about 1% to about 20%, more preferably from about 7% to about 14%, most preferably about 11% of the ester of palmitic acid.

Preferably the fluorescent naphthalimide diester dye is free of solvents even more preferably free of organic solvents.

Optionally, the fluorescent naphthalimide diester dye typically contains residual reactants and catalysts. Preferably the fluorescent naphthalimide diester dye contains less than from about 10%, preferably less than about 4%, alcohol which is the reaction product of residual fatty acid and epoxy compound, and less than from about 10%, preferably less than about 3%, unreacted epoxy compound. Preferably the fluorescent naphthalimide diester dye contains no unreacted fatty acid.

The Fluorescent Naphthalimide Diester Tracer

The "fluorescent naphthalimide diester tracer" comprises the fluorescent naphthalimide diester dye and a carrier. The carrier is an organic liquid, which is preferably compatible with, or the same as, an organic liquid used in the fluid system one intends to test. For example, the carrier may be: transmission fluid, hydraulic fluid, and engine oil, or lubricant from refrigerant system, or heating system. Such liquid carriers are for example polyalkylene glycols, polyolesters, mineral oil, polyalphaolefins, synthetic hydrocarbons refrigerant lubricants and refrigerants, liquid hydrocarbons, particularly hydrocarbon lubricants, motor oil, gear oil, transmission fluid, hydraulic fluid, synthetic oils, petroleum solvents.

The fluorescent naphthalimide diester tracer possess an increased stability in operation and storage, increased fluorescence strength, and thus increased visibility and effectiveness.

The fluorescent naphthalimide diester tracer is then administered into the fluid system, to detect leaks in the fluid system, using conventional techniques. The concentration of the fluorescent naphthalimide diester dye in the fluid system is preferably less than 1%, more preferably less than 0.01%, most preferably about 0.005%. While greater than 1% fluorescent naphthalimide diester dye is useful, it is typically not necessary and contributes to the cost.

The fluorescent naphthalimide diester dye can be applied directly to a bulk volume of a liquid that is utilized in the fluid system, such as a lubricant, at a concentration of preferably less than 1%, more preferably less than 0.01%, most preferably about 0.005%, so that the bulk of such lubricant becomes the carrier and the entire bulk volume carrier and fluorescent naphthalimide diester dye become the tracer. As a result, the fluorescent naphthalimide diester dye is administered along with the lubricant carrier when it is initially added to the system, or when the lubricant carrier is replenished or replaced.

The fluorescent naphthalimide diester dye may also be added to a smaller volume of carrier, typically at a concentration of from about 10% to about 20%; the fluorescent naphthalimide diester tracer is then administered to a fluid system, allowed to distribute through the fluid system and mix with the liquids such as lubricant, in the fluid system.

Whichever method of administration is employed, the fluid system is then inspected for leaks by scanning the exterior of the system with ultraviolet light inspecting the system for fluorescence which indicate a leak in the system.

Preparation of the Fluorescent Naphthalimide Diester Chromophore/Fluorescent Naphthalimide Diester Dye The fluorescent naphthalimide diester chromophore/fluorescent naphthalimide diester dye is prepared by: providing a naphthalimide diol; and reacting the hydroxyl groups of the naphthalimide diol with a fatty acid having from 8 to 24 carbon atoms in length, preferably from 12 to 22 carbon atoms in length, most preferably from 16 to 20 carbon atoms in length, and from 1 to 4 double bonds, most preferably 2 to 3 double bonds, to form fluorescent naphthalimide diester dye.

A suitable naphthalimide diol is Solvent Yellow 131, a 4-(3'-hydroxypropylaminoe)-n-(3"-hydroxypropyl)-naphthalimide, commercially available under the trade name Mohawk yellow dye from Day-Glo Color Corporation. The structure of Solvent Yellow 131 is shown below:

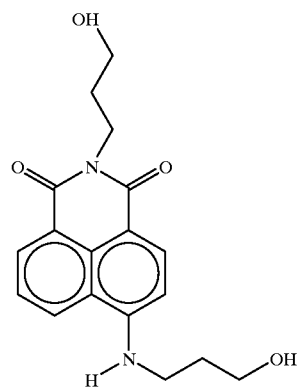

Next, the fatty acid is condensed onto the primary hydroxyl groups of the naphthalimide diol, preferably in the presence of a catalyst and an antioxidant. Good results have been obtained using a tin catalyst. A suitable tin catalyst is commercially available under the trade name Fascat 2001 from Atochem Company. A suitable antioxidant is commercially available under the trade name Irganox 1076 antioxidant from Ciba-Chemical Company.

Suitable linear fatty acids are for example: decanoic acid, nonanoic acid, octanoic acid, citronellic acid, undecanoic acid, lauric acid, tridecanoic acid, myristoleic acid, myristic acid, pentadecanoic acid, palmitoleic acid, palmitic acid, heptadecanoic acid, linolenic acid, linoleic acid, oleic acid, nonadecanoic acid, cis-11-eicosanoic acid, eicosanoic acid, 11, 14-eicosadienoic acid, erucic acid, docosanoic acid, and behenic acid. Suitable branched acids are for example: isononanoic acid, neoheptanoic acid, neononanoic acid, neodecanoic acid, iso-octanoic acid, neo octanoic acid, and isostearic acid.

An example of a suitable mixture of fatty acids typically contains about 3% myristic acid, about 1% margaric acid, about 2% stearic acid, about 2% myristoleic acid, about 1% linolenic acid, about 69% oleic acid, about 10% linoleic acid, about 6% palmitoleic acid, and about 6% palmitic acid. A suitable mixture is commercially available under the trade name "Industrene 105" from Witco Chemical Company. A similar mixture is commercially available under the trade name "Industrene 106" from Witco Chemical Company.

Another example of a suitable mixture fatty acids typically contains of about 4% stearic acid, about 24% oleic acid, about 53% linoleic acid, about 6% linolenic acid, and about 11% palmitic acid. A suitable mixture is commercially available under the trade name "Industrene 226" from Witco Chemical Company. A similar mixture is commercially available under the trade name "Ca 1700" from Chemical Associates Company.

Another example of a suitable mixture fatty acids typically contains of about 4.5% stearic acid, about 25.5% oleic acid, about 56% linoleic acid, about 7% linolenic acid, and about 7% palmitic acid. A suitable mixture is commercially available under the trade name "Industrene 225" from Witco Chemical Company.

Where a mixture of fatty acids is employed, the resulting fluorescent naphthalimide diester dye will contain a mixture of fluorescent naphthalimide diester chromophores.

The fatty acid—diol mixture is preferably heated above 170° C. or 180° C.; where the diol is 4-(3'-hydroxypropylaminoe)-n-(3"-hydroxypropyl)-naphthalimide, also known as Mohawk yellow dye, the fatty acid and diol is preferably heated to at least about 190° C.

to dissolve the Mohawk yellow dye. The mixture is preferably held at such elevated temperature for at least two hours, to get at least 90% reaction. Preferably the reaction is held 6 to 36 hours. Good results have been obtained by heating to 195° C. and maintaining that temperature for about six hours, such technique typically provides about 97% to 98% naphthalimide diester.

After reacting the diol and the fatty acid, an epoxy compound is optionally added and reacted for preferably from 2 hours to 24 hours preferably at from about 100° C. to about 160° C., more preferably at from about 130° C. to about 150° C. Good results have been obtained by reacting at 140° C. for six hours. Reaction temperatures at about 190° C. and higher are not preferred as such temperatures cause formation of a precipitate.

The epoxy compound is preferably a monofunctional or difunctional glycidyl ether or mixtures thereof, which is a liquid at room temperature preferably having a molecular weight of from about 130 to 300, more preferably from about 150 to about 250.

Suitable monofunctional epoxy compounds are for example, phenyl glycidyl ether (commercially available as Heloxy modifier 63), Alkyl $C_n$—$C_n$ glycidyl ethers (commercially available as Heloxy Modifier 7), Alkyl $C_n$—$C_n$ glycidyl ether(commercially available as Heloxy Modifier 8), Alkyl $C_n$—$C_n$ glycidyl ether (commercially available as Heloxy Modifier 9), Butyl glycidyl ether (commercially available as Heloxy Modifier 61), Cresyl glycidyl ether (commercially available as Heloxy Modifier 62), Phenyl glycidyl ether (commercially available as Heloxy Modifier 63), Nonylphenyl glycidyl ether (commercially available as Heloxy Modifier 64), p-tert-butylphenyl glycidyl ether (commercially available as Heloxy Modifier 65), 2-ethylhexyl glycidyl ether (commercially available as Heloxy Modifier 116) and a glycidyl ester of neodecanoic acid ) commercially available as Cardura E-10).

Suitable difunctional epoxy compounds are for example, diglycidyl ether of neopentyl glycol (commercially available as Heloxy modifier 68), digylcidyl ether of 1,4 butanediol (commercially available as Heloxy Modifier 67), diglycidyl ether of neopentyl glycol (commercially available as Heloxy Modifier 68), diglycidyl ether of cyclohexane dimethanol (commercially available as Heloxy Modifier 107, diglycidyl ether of dibromo neopentyl glycol (commercially available as Heloxy Modifier 56), polyglycol diepoxide (commercially available as Heloxy Modifier 32), and a dimer acid diglycidyl ester (commercially available as Heloxy Modifier 71). The Heloxy modifiers and the Cardura products are available from Shell Chemicals.

Trifunctional epoxy compounds are not preferred as they tend to precipitate. Good results have been obtained using about 1.9%, by weight of a phenyl glycidyl ether and 1.9%, by weight of diglycidyl ether of neopentyl glycol.

Preferably from 0% to about 10%, more preferably from about 0.01% to about 10%, even more preferably from about 2% to 6% by weight epoxy compound is added.

Upon completion of the reaction, the fluorescent naphthalimide diester dye is cooled, and preferably filtered. The fluorescent naphthalimide diester is then combined with a liquid preferably a liquid that is utilized in a fluid system to provide a fluorescent naphthalimide diester tracer.

EXAMPLE 1

A fluorescent yellow chromophore was synthesized by reacting 125 grams of Industrene 106 from Witco Chemical a fatty acid blend which is composed of oleic acid, linoleic acid, palmitoleic acid, and palmitic acid, with 73 grams of Mohawk yellow dye, 0.2 grams of Fascat 2001 tin catalyst, and 1.5 grams of Irganox 1076 antioxidant from Ciba-chemical company. The mixture was heated to 195° C. and held at that temperature for six hours. Upon completion of the reaction, the naphthalimide diester was cooled, filtered and tested in polyalkylene glycol for solubility and fluorescence. The resulting fluorescent naphthalamide diester dye was liquid at room temperature exhibited good solubility and fluorescence in polyalkylene glycol.

EXAMPLE 2

A fluorescent yellow chromophore was synthesized by reacting 150 grams of a fatty acid blend with 73 grams of Mohawk yellow dye, 0.2 grams of Fascat 2001 tin catalyst, and 1.5 grams of Irganox 1076 antioxidant from Ciba-chemical company. The fatty acid blend may be obtained as Hystrene 2290 from Witco chemical and is 90% Erucic acid by weight. The mixture was heated to 195° C. and held at that temperature for six hours. Upon completion of the reaction, the diester was cooled, filtered and tested in polyalkylene glycol for solubility and fluorescence. The resulting fluorescent naphthalamide diester dye was waxy at room temperature and exhibited good solubility and fluorescence in polyalkylene glycol.

EXAMPLE 3

A fluorescent yellow chromophore was synthesized by reacting 125 grams of Industrene 106 a fatty acid blend with 73 grams of Mohawk yellow dye, 0.2 grams of Fascat 2001 tin catalyst, and 1.5 grams of Irganox 1076 antioxidant from Ciba-chemical company. The mixture was heated to 195° C. and held at that temperature for six hours. Upon completion of the reaction, the diester was cooled, filtered and tested in polyalkylene glycol for solubility and fluorescence. The resulting fluorescent naphthalamide diester was liquid at room temperature and exhibited good solubility and fluorescence in polyalkylene glycol.

EXAMPLE 4

A fluorescent yellow chromophore was synthesized by reacting 569 grams of stearic acid with 325 grams of Mohawk yellow dye. The mixture was heated to 195° C. and held at that temperature for six hours. Upon completion of the reaction, the diester was cooled, filtered and tested in polyalkylene glycol for solubility and fluorescence. The resulting fluorescent naphthalamide diester dye was waxy at room temperature and exhibited good solubility and fluorescence in polyalkylene glycol.

EXAMPLE 5

A fluorescent yellow chromophore was synthesized by reacting 513 grams of palmitic acid with 325 grams of Mohawk yellow dye. The mixture was heated to 195° C. and held at that temperature for six hours. Upon completion of the reaction, the diester was cooled, filtered and tested in polyalkylene glycol for solubility and fluorescence. The resulting fluorescent naphthalamide diester dye was waxy at room temperature and exhibited good solubility and fluorescence in polyalkylene glycol.

EXAMPLE 6

A fluorescent yellow chromophore was synthesized by reacting 338 grams of a fatty acid blend with 211 grams of Mohawk yellow dye, 0.75 grams of Fascat 4201 tin catalyst, and 0.75 grams of magnesium oxide. The fatty acid blend may be obtained as Industrene 226 from Witco chemical and is composed of oleic, linoleic, linolenic, stearic, and palmitic acids. The mixture was heated to 195° C. and held at that temperature for 24 hours. After the 24-hour hold was complete, 20 grams of Araldit PT-810 Epoxy was added to the reaction and held at 195° C. for one hour. Upon completion of the reaction, the diester was cooled, filtered and tested in polyalkylene glycol for solubility and fluorescence. The resulting fluorescent naphthalamide diester dye was liquid at room temperature, had Mw of 2466 g/mole, an Mw/Mn ratio of 1.78 and Mn of 1382 g/mole and exhibited good solubility and fluorescence in polyalkylene glycol. The fluorescent naphthalamide diester dye is stable for more than 1000 hours of operation time.

EXAMPLE 7

A fluorescent yellow naphthalimide diester was synthesized by reacting 675 grams of a CA1700 fatty acid blend with 412 grams of Mohawk yellow dye and 1.5 grams of Fascat 4201 tin catalyst. The reaction was performed under a nitrogen gas inert atmosphere. The mixture was heated to 195° C. and held at that temperature for 24 hours. After the 24 hour hold was complete, the reaction was cooled to 140° C. upon which 18 grams of Heloxy modifier 68 and 18 grams of Heloxy modifier 63 was added to the reaction. The reaction was held at 140° C. for six hours. Upon completion of the reaction, the fluorescent naphthalimide diester diester dye was cooled, and filtered. The resulting fluorescent naphthalimide diester dye was liquid at room temperature and exhibited good solubility and fluorescence in polyalkylene glycol carrier.

The solubility of fluorescent naphthalimide diester dyes of the present invention was compared to conventional dyes in polyalkylene glycol carrier. Solutions of the fluorescent naphthalimide diester dyes and polyalkylene glycol, aromatic 200, hydraulic fluid and mineral oil were prepared in ratios of 20/80, 40/60 60/40 and 80/20 dye to carrier. The results are listed in Table 1. The chemical structures of the conventional naphthalimide chromophores are shown in FIG. 1.

TABLE 1

| Dye | Solubility in PAG | Solubility in Aromatic 200 | Solubility in Hydraulic Fluid | Solubility in Mineral Oil |
| --- | --- | --- | --- | --- |
| Acid Yellow 7 | <0.05 g | <0.05 g | <0.05 g | <0.05 g |
| Solvent Yellow 43 | <3.0 g | <3.0 g | <0.5 g | <0.5 g |
| Solvent Yellow 85 | <0.05 g | <0.05 g | <0.05 g | <0.05 g |
| Solvent Yellow 131 | <0.10 g | <0.05 g | <0.05 g | <0.05 g |
| Example 6 | 100% Miscible | 100% Miscible | 100% Miscible | 100% Miscible |
| Example 7 | 100 Miscible | 100% Miscible | 100% Miscible | 100% Miscible |

PAG — polyalkylene glycol, 100 grams

As shown from data in the table 1, the naphthalimide diester dye of examples of the present invention have improved solubility in organic solvents. The fluorescent the naphthalimide diester dye of examples 1 to 5 displayed good solubility in polyalkylene glycol, fair solubility in other aromatic 200, hydraulic fluid and mineral oil. However, the fair solubility in aromatic 200, hydraulic fluid and mineral oil was better than the solubility of the comparative dyes, the acid yellow 7, solvent yellow 43, solvent yellow 85, and solvent yellow 131.

What is claimed is:
1. A naphthalimide diester chromophore having the following structure:

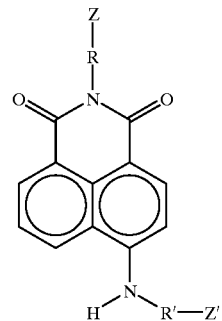

wherein:
Z and Z', are the same or different, and each is an ester having a saturated or unsaturated, linear or branched, hydrocarbon chain attached thereto, having from 8 to 24 carbon atoms in length, and from 1 to 4 double bonds;
R and R' are the same or different and each is a saturated, linear hydrocarbon chain, having from 2 to 10 carbon atoms in length; and
wherein the naphthalimide diester is prepared by reacting naphthalimide diol with a fatty acid.
2. The naphthalimide diester of claim 1 where R and R' have from 2 to 8 carbon atoms, and Z and Z' have from 12 to 22 carbon atoms.
3. The naphthalimide diester of claim 1 where Z and Z' have from 16 to 20 carbon atoms.
4. The naphthalimide diester of claim 1, where Z or Z' or both are selected from the group consisting of: deconaoic acid, noanoic acid, octanoic acid, citronellic acid, undecanoic acid, lauric acid, tridecanoic acid, myristoleic acid, myristic acid, pentadecanoic acid, palmitoleic acid, palmitic acid, heptadacanoic acid, linolenic acid, linoleic acid, oleic acid, nonadecanoic acid, cis-11-eicosanoic acid, eicosanoic acid, 11, 14-eicosadienoic acid, erucic acid, docosanoic acid, behenic acid, isononanoic acid, neoheptanoic acid, neononanoic acid, neodecanoic acid, iso-octanoic acid, neo octanoic acid, isostearic acid and mixtures thereof.
5. The naphthalimide diester of claim 1, wherein Z or Z' or both are selected from the group consisting of: the ester of oleic acid, the ester of linoleic acid, the ester of linolenic acid and mixtures thereof.
6. The naphthalimide diester of claim 5, where Z or Z' or both are linoleic acid.
7. The naphthalimide diester of claim 5, where Z or Z' or both are linolenic acid.

8. The naphthalimide diester of claim 5, where Z or Z' or both are oleic acid.

9. A naphthalimide diester dye composition which comprises a naphthalimide diester chromophore having the following structure:

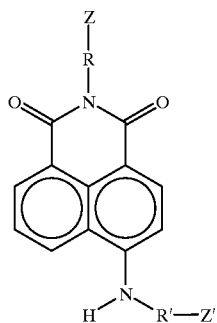

wherein:
Z is an ester and Z' is an ester having a saturated or unsaturated, linear or branched, hydrocarbon chain attached thereto, having from 8 to 24 carbon atoms in length, and from 1 to 4 double bonds
R and R' are saturated, linear hydrocarbon chains, having from 2 to 10 carbon atoms in length; and
wherein the naphthalimide diester is prepared by reacting naphthalimide diol with a fatty acid.

10. The naphthalimide diester dye composition of claim 9 further comprising a second chromophore having the following structure:

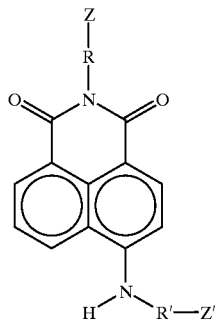

wherein:
Z is an ester and Z' is an ester having a saturated or unsaturated, linear or branched, hydrocarbon chain attached thereto, having from 8 to 24 carbon atoms in length, and from 1 to 4 double bonds; and
R and R' are saturated, linear hydrocarbon chains, having from 2 to 10 carbon atoms in length.

11. The naphthalimide diester dye composition of claim 10 where R and R' have from 2 to 8 carbon atoms, and Z and Z' have from 12 to 22 carbon atoms.

12. The naphthalimide diester dye composition of claim 10 where Z and Z' have from 16 to 20 carbon atoms.

13. The naphthalimide diester dye composition of claim 10, where Z or Z' or both are selected from the group consisting of: decanoic acid, nonanoic acid, octanoic acid, citronellic acid, undecanoic acid, lauric acid, tridecanoic acid, myristoleic acid, myristic acid, pentadecanoic acid, palmitoleic acid, palmitic acid, heptadecanoic acid, linolenic acid, linoleic acid, oleic acid, nonadecanoic acid, cis-11-eicosanoic acid, eicosanoic acid, 11, 14-eicosadienoic acid, erucic acid, docosanoic acid, behenic acid, isononanoic acid, neoheptanoic acid, neononanoic acid, neodecanoic acid, iso-octanoic acid, neo octanoic acid, isostearic acid and mixtures thereof.

14. The naphthalimide diester dye composition of claim 10, where Z or Z' or both are selected from the group consisting of: the ester of oleic acid, the ester of linoleic acid, the ester of linolenic acid and mixtures thereof.

15. The naphthalimide diester dye composition of claim 14, where Z or Z' or both are linoleic acid.

16. The naphthalimide diester dye composition of claim 14, where Z or Z' or both are linolenic acid.

17. The naphthalimide diester dye composition of claim 14, where Z or Z' or both are oleic acid.

18. The naphthalimide diester dye composition of claim 9, wherein said dye lacks organic solvent.

19. The naphthalimide diester dye composition of claim 10, wherein R and R' have 3 carbon atoms, and the dye contains a mixture of chromphores, wherein Z of the mixture comprise: an ester of oleic acid, ester of linoleic acid, ester of liolenic acid, ester of palmitic acid and ester of stearic acid; wherein Z' of the mixture comprise: ester of oleic acid, ester of linoleic acid, ester of liolenic acid, ester of palmitic acid and ester of stearic acid.

20. A fluorescent tracer comprising:

(a) a naphthalimide diester dye composition comprising a naphthalimide diester chromophore having the following structure:

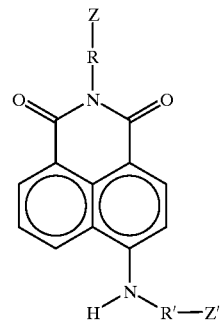

wherein:

Z is and ester and Z' is an ester having a saturated or unsaturated, linear or branched, hydrocarbon chain attached thereto, having from 8 to 24 carbon atoms in length, and from 1 to 4 double bonds;

R and R' are saturated, linear hydrocarbon chains, having from 2 to 10 carbon atoms in length;

wherein the naphthalimide diester is prepared by reacting naphthalimide diol with a fatty acid; and (b) a carrier.

21. The tracer of claim 20, wherein the carrier is selected from the group consisting of: polyalkylene glycols, polyolesters, mineral oil, polyalphaolefins, synthetic hydrocarbons refrigerant lubricants and refrigerants, liquid hydrocarbons, particularly hydrocarbon lubricants, motor oil, gear oil, transmission fluid, hydraulic fluid, synthetic oils, petroleum solvents and mixtures thereof.

22. A method for preparing a naphthalimide diester chromophore comprising:

reacting a naphthalimide diol with a fatty acid having from 8 to 24 carbon atoms to form a naphthalimide diester chromophore having the following structure:

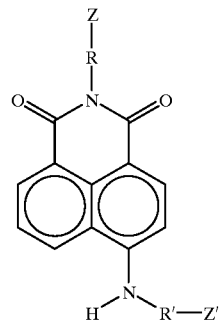

wherein:

Z is an ester and Z' is an ester having a saturated or unsaturated, linear or branched, hydrocarbon chain attached thereto, having from 8 to 24 carbon atoms in length, and from 1 to 4 double bonds; and R and R' are saturated, linear hydrocarbon chains, having from 2 to 10 carbon atoms in length.

23. A fluid system containing a naphthalimide diester chromphore of claim 1.

* * * * *